United States Patent [19]

Fake

[11] 4,224,331
[45] Sep. 23, 1980

[54] DERIVATIVES OF 2-PYRIDYLTHIOUREA AND PHARMACEUTICAL COMPOSITIONS

[75] Inventor: Charles S. Fake, Harlow, England

[73] Assignee: Beecham Group Limited, England

[21] Appl. No.: 570,015

[22] Filed: Apr. 21, 1975

Related U.S. Application Data

[62] Division of Ser. No. 438,562, Feb. 1, 1974, abandoned.

[30] Foreign Application Priority Data

Feb. 17, 1973 [GB] United Kingdom ................. 7933/73

[51] Int. Cl.² ............................................. A61K 31/44
[52] U.S. Cl. .................................................... 424/263
[58] Field of Search ........................................ 424/263

[56] References Cited

U.S. PATENT DOCUMENTS

| | | | |
|---|---|---|---|
| 3,467,753 | 9/1969 | Foster et al. | 424/263 |
| 3,736,331 | 5/1973 | Black et al. | 424/263 |
| 3,908,014 | 9/1975 | Durant et al. | 424/263 |

FOREIGN PATENT DOCUMENTS

| | | | |
|---|---|---|---|
| 2040374 | 11/1969 | Fed. Rep. of Germany | 424/263 |
| 46-12447 | 3/1971 | Japan | 424/263 |

*Primary Examiner*—Frederick E. Waddell
*Attorney, Agent, or Firm*—Jacobs & Jacobs

[57] ABSTRACT

Orally administrable pharmaceutical compositions for reducing the rate of gastric acid secretion and acid addition salts thereof containing an effective amount of halo-substituted 2-pyridyl thioureas and a pharmaceutical carrier and a method of treating gastric ulcers and reducing gastric acid secretion with such compositions.

3 Claims, No Drawings

DERIVATIVES OF 2-PYRIDYLTHIOUREA AND PHARMACEUTICAL COMPOSITIONS

This application is a division of application Ser. No. 438,562 filed Feb. 1, 1974, now abandoned.

SUMMARY OF THE INVENTION

Pharmaceutical compositions useful for the reduction of gastric acid secretion are provided which compositions comprise a compound of the formula $$Py-NH-CS-NR_5R_6$$

wherein Py is a 2-pyridyl group which may be substituted by one or more methyl groups or chlorine or bromine atoms and $R_5$ is a hydrogen atom or a group $R_7$ or $CO.R_7$ where $R_7$ is a methyl, ethyl, propyl, phenyl, benzyl or such a group substituted by a hydroxyl group; $R_6$ is a hydrogen atom or a methyl or ethyl group or is joined to $R_5$ so that the $NR_5R_6$ group is a cyclic group or 3-6 members and acid addition salts thereof; together with a conventional pharmaceutical carrier.

Many of the above compounds are novel and their preparation is described.

This invention relates to certain pyridylthioureas which have a beneficial effect on gastric secretion rates.

The class of compounds of the formula (I):

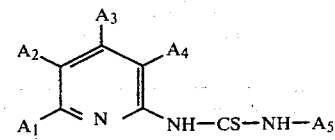

wherein $A_1$ is hydrogen or methyl, $A_2$ is hydrogen, methyl, bromine or chlorine, $A_3$ is hydrogen or methyl, $A_4$ is hydrogen, methyl, bromine or chlorine and $A_5$ is hydrogen or benzoyl was referred to in a general manner in British Pat. No. 1,267,433 as suitable intermediates in the preparation of certain pharmaceutically active imidazolines. The compounds of formula (I) were not then thought to have any pharmacological activity. It has now been found that certain of the thioureas for formula (I) and related thioureas possess beneficial pharmacological properties and in particular reduce the rate of gastric acid secretion and reduce the incidence of gastric ulceration.

Accordingly, the present invention provides a pharmaceutical composition comprising a compound of the formula (II):

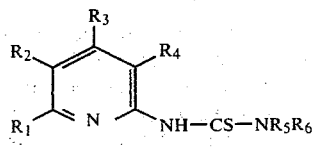

wherein $R_1$ is a hydrogen atom or a methyl group; $R_2$ is a hydrogen, chlorine or bromine atom or a methyl group; $R_3$ is a hydrogen atom or a methyl group; $R_4$ is a hydrogen, chlorine or bromine atom or a methyl group; $R_5$ is a hydrogen atom or a group $R_7$ or $CO.R_7$ where $R_7$ is a methyl, ethyl, propyl, phenyl, benzyl or such a group substituted by a hydroxyl group; $R_6$ is a hydrogen atom or a methyl or ethyl group or is joined to $R_5$ so that the $NR_5R_6$ group is a cyclic group or 3-6 members and acid addition salts thereof; together with a conventional pharmaceutical carrier.

Most suitably, $R_1$ is a hydrogen atom; $R_3$ is a hydrogen atom and at least one of $R_2$ and $R_4$ is a halogen atom.

Preferably $R_2$ is a halogen atom.

Suitable cyclic groups $NR_5R_6$ include the pyrollidine, piperidine, morpholine, piperazine or N-methyl piperazine groups.

Most suitably, $R_5$ is a hydrogen atom or a methyl or ethyl group.

Most suitably, $R_6$ is a hydrogen atom or a methyl or ethyl group.

One particularly preferred group of compounds for use in the compositions of this invention are those of the formula (III):

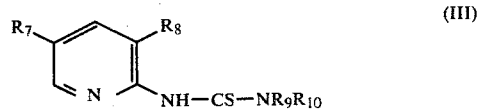

and acid addition salts thereof wherein $R_7$ is a hydrogen, chlorine or bromine atom; $R_8$ is a hydrogen, chlorine or bromine atom; $R_9$ is a hydrogen atom or methyl or ethyl group and $R_{10}$ is a hydrogen atom or a methyl or ethyl group.

Most suitably, $R_7$ is a chlorine or bromine atom.

Most suitably, $R_8$ is a hydrogen or chlorine atom.

Preferably $R_7$ and $R_8$ are both chlorine atoms.

Most suitably, $R_9$ is a hydrogen atom.

Preferred compounds for inclusion in the compositions of the invention are 1-(3,5-dichloro-2-pyridyl)-3-methyl-2-thiourea and (3,5-dichloro-2-pyridyl)thiourea or a salt thereof.

If desired, the compound of formula (II) may be present in the form of an acid addition salt with a conventional pharmaceutically acceptable acid such as hydrochloric, hydrobromic, phosphonic, acetic, fumaric, salicylic, citric, lactic, mandelic, tartaric, methylsulphonic or the like but it is often preferable that the active compound is present as the free base.

The compositions of the invention may be in a form suitable for oral or parenteral administration although orally administrable forms are generally preferred.

The pharmaceutical compositions may be solid, such as tablets, pills, coated pills, suppositories, and capsules or liquids such as solutions, suspensions or emulsions.

The carriers may be conventional organic or inorganic substances, such as starch, magnesium stearate, talc, stearine, water, polyalkylene glycols and magnesium carbonate. The pharmaceutical compositions may contain additives, such as emulsifying, stabilizing, disintegrating and wetting agents.

The pharmaceutical compositions of the present invention may be prepared by usual methods of the pharmaceutical industry known per se, by admixing the active ingredient with suitable solid or liquid organic or inorganic pharmaceutical carriers and/or excipients and, if desired, with other therapeutically active compounds.

The compositions of the invention may be administered to mammals to reduce the secretion of gastric acid and to prevent formation of or to help the healing of gastric ulcers. Suitable daily dosage ranges are from 1 to 50 mg/kg. preferably in divided doses. Suitable individual oral dosage forms contains from 10 to 800 mgs. of active material, for example, from 25 to 500 mgs.

Certain compounds of formula (II) are novel and as such form a part of this invention. These compounds include those of formula (II) wherein $R_1$, $R_2$, $R_3$, $R_4$, $R_5$ and $R_6$ are as defined in relation to formula (II) except that (a) $R_6$ is not hydrogen when $R_5$ is hydrogen or β-hydroxyethyl and (b) $R_1$, $R_2$, $R_3$ and $R_4$ are not all hydrogen.

The most suitable and preferred new compounds are those which fall within the definitions of the most suitable and preferred compounds for inclusion in the compositions of the invention.

Compounds of the formula (II) may be prepared by the reaction of an amine of the formula $HNR_5R_6$ upon an isothiocyanate of the formula

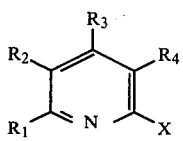
(IV)

a, X is N=C=S
b, X is NH . CS . NH
c, X is NH . CS . NH . CO . $C_6H_5$
d, X is $NH_2$
e, X is NH . CS . $SCH_2Ph$ in an inert solvent at a non-extreme temperature. Suitable solvents include chloroform, ethanol, dioxane, dimethylformamide, benzene, ethylacetate and the like. The reaction may be carried out at $-20°$ to $+200°$ C. but temperatures in the range $5°-100°$ C. are generally sufficient and ambient temperatures are preferred.

The isothiocyanates of formula (IVa) may be prepared by the thermal decomposition of the corresponding unsubstituted thiourea of formula (IVb) in conventional manner, for example, by heating in chlorobenzene. The thioureas of formula (IVb) may be prepared by the general procedures described in British Pat. No. 1,267,433, for example, by debenzoylation of the N-benzoylthiourea of formula (IVc) formed by the reaction of benzoyl isothiocyanate and the appropriate 2-aminopyridine of formula (IVd).

If desired, the thiourea of formula (II) may be prepared from the corresponding thiourea of formula (IVb) by heating that compound in the presence of an amine $HNR_5R_6$. Such a reaction generally takes place in a high boiling solvent such as chlorobenzene or in a bomb if the amine $HNR_5R_6$ has a boiling point below about 110° C. Presumably the reaction proceeds via the isothiocyanate of the formula (IVa).

Compounds of formula (II) wherein $R_5$ is a hydrogen atom may be prepared by the reaction of a 2-aminopyridine of formula (IVa) with an isothiocyanate of formula $R_6NCS$. The reaction conditions for such a condensation will be similar to those described for the reaction of the pyridylisothiocyanate (IVc) and an amine $HNR_5R_6$.

An advantageous method of preparing isothiocyanates of formula (IVa) is by the reaction of the corresponding pyridine (IVd) with thiophosgene in an inert solvent such as toluene.

A further method suitable for producing compounds of formula (II) is by the reaction of an amine $HNR_5R_6$ and a dithiocarbamate of the formula (IVe). Such a reaction is normally carried out in ethanolic solution at ambient temperature or under reflux. This reaction does not usually give good yields when $R_2$ and $R_4$ are both halogen atoms.

The following Examples illustrate the invention:

EXAMPLE 1

1-(3,5-Dichloro-2-pyridyl)-3-methyl-2-thiourea (a) 3,5-Dichloro-2-pyridylisothiocyanate 3,5-Dichloro-2-amino pyridine (8.15, 0.05 mol) was treated with thiophosgenes (10% soln. in toluene, 55 ml). The mixture was refluxed until clear solution was obtained and no further hydrochloric acid gas was being evolved. The mixture was cooled, and the solid which crystallised was removed by filtration. The mother liquors, after evaporation and crystallisation of the residual oil, yielded 5.5 g. (55%) of the required isothiocyanate as pale yellow needles m. pt. $45°-6°$.

(b) 1-(3,5-Dichloro-2-pyridyl)-3-methyl-2-thiourea

A solution of 3,5 dichloro-2-pyridylisothiocyanate (5.13 g.) in benzene (20 ml.) was added to a solution of methylamine in ethanol (5 ml., 33%) and the mixture was stirred for 18 hours at ambient temperature. Petroleum ether (60°-80° C., 30 ml.) was added and the resulting precipitate was filtered off and recrystallised from benzene-light petroleum to give colourless microcrystals of 1-(3,5-dichloro-2-pyridyl)-3-methyl-2-thiourea (4.18 g.) m.pt. 105°-109° C.

EXAMPLES 2-15

Using the procedure of Example 1, the following compounds of formula (II) may be prepared:

| $R_1$ | $R_2$ | $R_3$ | $R_4$ | $NR_5R_6$ | m.pt. °C. |
|---|---|---|---|---|---|
| H | H | H | H | $NHCH_2C_6H_5$ | 160 |
| H | H | H | H | ⟨N O⟩ (morpholino) | 101 |
| H | Br | H | H | $NHCH_3$ | 224 |
| H | Cl | H | H | $NHCH_3$ | 214 |
| H | Cl | H | H | $NHC_2H_5$ | 177 |
| H | Cl | H | H | $N(CH_3)_2$ | 130 |
| H | Cl | H | H | $NH_2$ | 234 |
| H | H | $CH_3$ | H | $NHCH_3$ | 175 |
| H | $CH_3$ | H | H | $NHCH_3$ | 161 |
| $CH_3$ | H | H | H | $NHCH_3$ | 201-2 |
| H | $CH_3$ | H | H | N⟨$CH_2$/$CH_2$⟩ | 52 |
| H | Cl | Cl | H | $NHC_6H_5$ | 131 |
| H | Cl | Cl | H | $NHCH_2C_6H_5$ | 84 |
| $CH_3$ | H | $CH_3$ | H | $NHCH_3$ | 172 |

EXAMPLE 16

In the pyloric ligated administration of the compound of Example 1 at a dose of 50 mg/kg. subcutaneously or less than 10 mg/kg. intraduodenally was found to reduce the volume of gastric secretion by approximately 50%. At an oral dose of 25 mg/kg., this compound also inhibited the formation of 6 hour stress induced ucler in the rat [Method of Takagi and Okabe, Jap. J. Pharmacol., 18, 9-18 (1968)].

EXAMPLE 17

The following ingredients were milled, screened, mixed and filled into a hard gelatin capsule 1-(3,5-Dichloro-2-pyridyl)-3-methyl-2-thiourea: 100 mg.

Sucrose: 120 mg.
Starch: 28 mg.
Magnesium Stearate: 2 mg.

EXAMPLE 18

The following ingredients were milled, screened, mixed and filled into a hard gelatin capsule
3,5-Dichloro-2-pyridylthiourea: 50 mg.
Lactose: 50 mg.

EXAMPLE 19

1-(5-Methyl-2-pyridyl)-3-methylthiourea (a) Benzyl-(5-methyl-2-pyridyl)dithiocarbamate 2-Amino-5-methylpyridine (21.6 g., 0.2 mol.) was suspended in triethylamine (60 ml.) and carbon disulphide (30 ml.) was added. The mixture was shaken at room temperature for 3 hours. The pale yellow solid precipitate was filtered off and washed with ether to give 5-methyl-2-pyridyldithiocarbamic acid triethylamine salt (37.7 g., 66%). This material was suspended in ethanol (100 ml.) and stirred at room temperature. Benzyl chloride (16.5 g., 15 ml.) was added dropwise. After 2 hours, a clear solution was obtained. Water was added and the precipitated benzyl ester collected. After washing with water and petrol ether (40°–60° C.), the product weighed 33.8 g. (m.pt. 141° C.).

(b) 1-(5-Methyl-2-pyridyl)-3-methylthiourea

Benzyl(5-methyl-2-pyridyl)dithiocarbamate (3 g.) was suspended in ethanol (30 ml.). Methylamine (33% ethanolic solution, 10 ml.) was added and the mixture stirred at room temperature for 1 hour. On the addition of water, the thiourea separated and was collected by filtration, dried and recrystallised from ethanol-petrol ether. Yield 2.5 g., m.pt. 161° C.

What is claimed is:

1. A method of treating gastric ulcers or reducing gastric acid secretion which comprises orally administering to a subject in need thereof a therapeutically effective amount of a composition which comprises a therapeutically effective amount of a compound of formula (III):

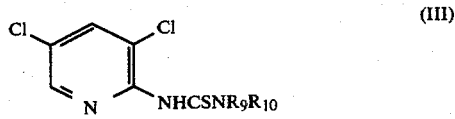

or a pharmaceutically acceptable acid addition sale thereof, wherein $R_9$ and $R_{10}$ are each hydrogen, methyl or ethyl in combination with a pharmaceutically acceptable carrier.

2. A method according to claim 1, wherein the compound of formula (III) in the composition is 1-(3,5-dichloro-2-pyridyl)-3-methyl-2-thiourea.

3. A method according to claim 1, wherein the compound of formula (III) in the composition is (3,5-dichloro-2-pyridyl) thiourea.